United States Patent
Nagano et al.

(10) Patent No.: US 8,648,190 B2
(45) Date of Patent: Feb. 11, 2014

(54) PROCESS FOR PRODUCING 2-HYDROXYMETHYLMORPHOLINE SALT

(75) Inventors: Yoshifumi Nagano, Osaka (JP); Keisuke Yaegashi, Yamaguchi (JP); Shingo Iwashina, Osaka (JP)

(73) Assignee: Daiso Co., Ltd., Osaka (JP)

( * ) Notice: Subject to any disclaimer, the term of this patent is extended or adjusted under 35 U.S.C. 154(b) by 160 days.

(21) Appl. No.: 13/144,202

(22) PCT Filed: Jan. 15, 2010

(86) PCT No.: PCT/JP2010/050415
§ 371 (c)(1),
(2), (4) Date: Oct. 4, 2011

(87) PCT Pub. No.: WO2010/082627
PCT Pub. Date: Jul. 22, 2010

(65) Prior Publication Data
US 2012/0016120 A1    Jan. 19, 2012

(30) Foreign Application Priority Data
Jan. 16, 2009    (JP) ................................ 2009-007282

(51) Int. Cl.
*C07D 265/10*    (2006.01)

(52) U.S. Cl.
USPC ........................................ 544/170; 540/544

(58) Field of Classification Search
USPC ....................................................... 544/170
See application file for complete search history.

(56) References Cited

U.S. PATENT DOCUMENTS

2007/0082931 A1    4/2007    Ratcliffe et al.

FOREIGN PATENT DOCUMENTS

| JP | 04-120081 A | 4/1992 |
| WO | WO 2005/068460 A1 | 7/2005 |
| WO | WO 2007/023143 A1 | 3/2007 |
| WO | WO 2008/070150 A1 | 6/2008 |

OTHER PUBLICATIONS

Jinbo et al., *J. Med. Chem.*, 37(17): 2791-2796 (1994).
Loftus, F., *Synthetic Communications*, 10(1): 59-73 (1980).
European Patent Office, Extended European Search Report in European Patent Application No. 10731296.9-2101 (Jul. 4, 2012).
Berg et al., *J. Med. Chem.*, 41(11): 1934-1942 (1998).
Breuning et al., *Eur. J. Org. Chemistry*, 13: 2100-2106 (2007).
Buriks et al., *J. Org. Chem.*, 52(23): 5247-5254 (1987).
Henegar, Kevin, *J. Org. Chem.*, 73(9): 3662-3665 (2008) and Supporting Information.
Japanese Patent Office, International Search Report in International Application No. PCT/JP2010/050415 (Mar. 23, 2010).
Japanese Patent Office, Written Opinion in International Application No. PCT/JP2010/050415 (Mar. 23, 2010).

*Primary Examiner* — Kahsay Habte
(74) *Attorney, Agent, or Firm* — Leydig, Voit & Mayer, Ltd.

(57) ABSTRACT

The invention relates to a production method of a 2-hydroxymethylmorpholine salt, which includes crystallization from a solution containing 2-hydroxymethylmorpholine of formula (1)

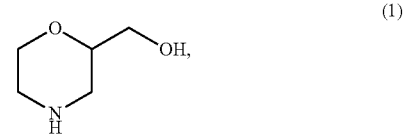

(1)

1,4-oxazepane compound of formula (2)

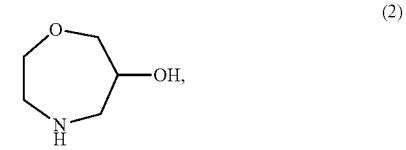

(2)

and an acid.

13 Claims, No Drawings

PROCESS FOR PRODUCING 2-HYDROXYMETHYLMORPHOLINE SALT

TECHNICAL FIELD

The present invention relates to a production method of a 2-hydroxymethylmorpholine salt useful as a synthetic intermediate for pharmaceutical products, agricultural chemicals and the like.

BACKGROUND ART

2-Hydroxymethylmorpholine is widely used as an intermediate for pharmaceutical products, agricultural chemicals and the like, for example, a synthetic intermediate for CNS compounds such as reboxetine, which is an antidepressant, and the like.

The following method is known as a production method of 2-hydroxymethylmorpholine.

By reacting epichlorohydrin with N-benzylethanolamine, N-benzyl-2-(hydroxymethyl)morpholine containing a 1,4-oxazepane compound is obtained. Then, this is reacted with succinic anhydride at −25° C., and the crude product is extracted with aqueous ammonia to give a hemisuccinate compound of N-benzyl-2-(hydroxymethyl)morpholine. This is further hydrolyzed with aqueous sodium hydroxide solution and extracted with an organic solvent to give N-benzyl-2-(hydroxymethyl)morpholine, which is subjected to a hydrogenation reaction using a palladium catalyst to perform debenzylation, whereby 2-hydroxymethylmorpholine is obtained (non-patent document 1).

However, in the above-mentioned method, removal of impurity (1,4-oxazepane compound) is achieved by once reacting succinic anhydride with N-benzyl-2-(hydroxymethyl)morpholine to lead to a hemisuccinate compound, performing a partitioning treatment, removing the impurity and hydrolyzing the hemisuccinate compound by an alkali treatment. As a result, the reaction steps are extremely long, and therefore, the method is complicated and impractical for industrial scale. In addition, since large amounts of aqueous ammonia and organic solvents are used to remove the impurity (1,4-oxazepane compound), the method is costly and low in efficiency. Furthermore, the reaction with succinic anhydride requires an industrially special low temperature facility to set to −25° C., and the method is not industrially suitable.

In addition, since 2-hydroxymethylmorpholine is a tacky gummy substance (non-patent document 1) which is difficult to handle, distribution thereof as an industrial product is difficult.

Patent document 1 describes that racemic 2-hydroxymethylmorpholine trifluoroacetate, which is a synthetic intermediate for pharmaceutical products, is obtained as a tacky oily substance.

Patent documents 2 and 3 describe that racemic 2-hydroxymethylmorpholine hydrochloride is obtained as a synthetic intermediate for pharmaceutical products. However, the properties thereof are not described.

These documents do not describe an optically active 2-hydroxymethylmorpholine salt.

DOCUMENT LIST

Patent Documents patent document 1: WO2008/070150
patent document 2: JP-A-4-120081
patent document 3: WO2005/068460

Non-Patent Document non-patent document 1: J. Org. Chem., 73, 3662-3665 (2008) and Supporting Information thereof

SUMMARY OF THE INVENTION

Problems to be Solved by the Invention

In view of the above-mentioned situation, the present invention aims to provide a more convenient and more efficient production method of a 2-hydroxymethylmorpholine salt, and further, to provide an easily handleable solid 2-hydroxymethylmorpholine salt.

Means of Solving the Problems

The present inventors have conducted intensive studies in an attempt to solve the aforementioned problems and found that the object 2-hydroxymethylmorpholine salt can be conveniently obtained as an easily handleable solid with high purity by crystallizing a salt formed by a composition containing 2-hydroxymethylmorpholine and impurities such as a 1,4-oxazepane compound and the like together with an inorganic acid such as hydrochloric acid, sulfuric acid and the like, a carboxylic acid such as acetic acid, trifluoroacetic acid and the like or a sulfonic acid such as benzenesulfonic acid, p-toluenesulfonic acid and the like.

The present invention has been completed based on the above-mentioned finding, and provides a production method of a 2-hydroxymethylmorpholine salt, and further, a novel acid addition salt of optically active 2-hydroxymethylmorpholine, which are shown below.

[1] A method of producing a 2-hydroxymethylmorpholine salt, comprising crystallizing the salt from a solution containing 2-hydroxymethylmorpholine represented by the following formula (1)

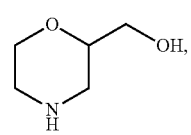

(1)

1,4-oxazepane compound represented by the following formula (2)

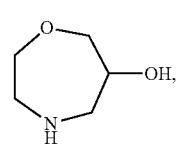

(2)

and an acid.

[2] The production method of the above-mentioned [1], wherein the 2-hydroxymethylmorpholine salt is represented by the formula (3)

(3)

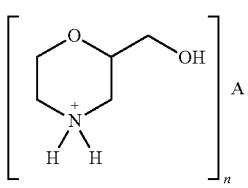

wherein A is an acidic counter anion, and n is an integer of 1 or 2.

[3] The production method of the above-mentioned [1] or [2], comprising mixing a composition containing the 2-hydroxymethylmorpholine represented by the formula (1) and the 1,4-oxazepane compound represented by the formula (2) with an acid to allow crystallization.

[4] The production method of the above-mentioned [3], wherein the composition containing the 2-hydroxymethylmorpholine represented by the formula (1) and the 1,4-oxazepane compound represented by the formula (2) is obtained by reacting an epihalohydrin represented by the following formula (4)

(4)

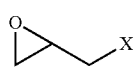

wherein X is a chlorine atom or a bromine atom, with an N-protected ethanolamine represented by the formula (5)

(5)

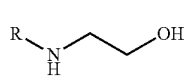

wherein R is a protecting group selected from a $C_{1-6}$ alkyl group, an allyl group and a benzyl group, to give a reaction composition containing an N-protected 2-hydroxymethylmorpholine represented by the following formula (8)

(8)

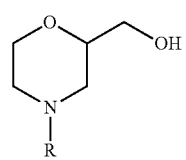

wherein R is as defined above, and an N-protected 1,4-oxazepane compound represented by the following formula (9)

(9)

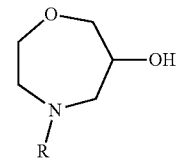

wherein R is as defined above, and then subjecting the reacting composition to deprotection to remove R.

[5] The production method of the above-mentioned [1] or [2], which comprises a step of subjecting a composition containing an N-protected 2-hydroxymethylmorpholine represented by the following formula (8)

(8)

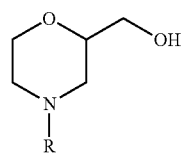

wherein R is a protecting group selected from a $C_{1-6}$ alkyl group, an allyl group and a benzyl group, and an N-protected 1,4-oxazepane compound represented by the following formula (9)

(9)

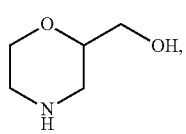

wherein R is as defined above, to deprotection in the presence of an acid to remove R to give a reaction composition containing 2-hydroxymethylmorpholine represented by the following formula (1)

(1)

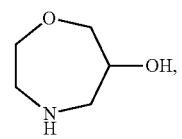

1,4-oxazepane compound represented by the following formula (2)

(2)

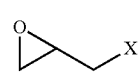

and an acid, and then allowing crystallization.

[6] The production method of the above-mentioned [5], wherein the composition containing the N-protected 2-hydroxymethylmorpholine represented by the formula (8) and the N-protected 1,4-oxazepane compound represented by the formula (9) is obtained by reacting an epihalohydrin represented by the following formula (4)

(4)

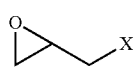

wherein X is a chlorine atom or a bromine atom, with an N-protected ethanolamine represented by the formula (5)

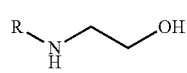 (5)

wherein R is a protecting group selected from a $C_{1-6}$ alkyl group, an allyl group and a benzyl group.

[7] The production method of any one of the above-mentioned [1] to [6], wherein the aforementioned acid is selected from an inorganic acid, a carboxylic acid and a sulfonic acid.

[8] The production method of the above-mentioned [7], wherein the aforementioned acid is selected from hydrogen fluoride, hydrogen chloride, hydrogen bromide, hydrogen iodide, sulfuric acid and nitric acid.

[9] The production method of the above-mentioned [7], wherein the aforementioned acid is selected from formic acid, acetic acid, propionic acid, butyric acid, pivalic acid, chloroacetic acid, trichloroacetic acid, trifluoroacetic acid, oxalic acid, benzoic acid, p-nitrobenzoic acid, fumaric acid, maleic acid and terephthalic acid.

[10] The production method of the above-mentioned [7], wherein the aforementioned acid is selected from methanesulfonic acid, trifluoromethanesulfonic acid, benzenesulfonic acid, p-toluenesulfonic acid and camphorsulfonic acid.

[11] The production method of any one of the above-mentioned [1] to [10], wherein the salt is crystallized from a solution of at least one kind of solvent selected from water, alcohol solvents, ether solvents, aromatic hydrocarbon solvents, aliphatic hydrocarbon solvents, halogen solvents, ester solvents, ketone solvents and nitrile solvents.

[12] The production method of the above-mentioned [11], wherein the salt is crystallized from a solution of an ester solvent.

[13] The production method of any one of the above-mentioned [4] to [6], wherein R is a benzyl group.

[14] The production method of any one of the above-mentioned [1] to [13], wherein the 2-hydroxymethylmorpholine salt is an optically active form.

[15] An acid addition salt of optically active 2-hydroxymethylmorpholine.

[16] The acid addition salt of the above-mentioned [15], which is selected from p-nitrobenzoate, fumarate, maleate, terephthalate, oxalate and trifluoroacetate.

[17] The acid addition salt of the above-mentioned [15], which is represented by the following formula (3)

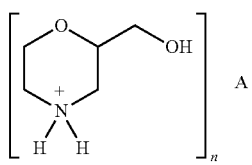 (3)

wherein A is p-nitrobenzoic anion (n is 1), fumaric anion (n is 1 or 2), maleic anion (n is 1 or 2), terephthalic anion (n is 1 or 2), oxalic anion (n is 1 or 2) or trifluoroacetic anion (n is 1).

[18] The acid addition salt of any one of the above-mentioned [15] to [17], which is a crystal.

[19] A crystal of optically active 2-hydroxymethylmorpholine trifluoroacetate showing characteristic peaks at diffraction angles 2θ of about 15.93°, 18.86°, 20.48°, 21.34°, 28.47° and) 29.61° (each ±0.2° in powder X-ray diffraction spectrum.

[20] A crystal of optically active 2-hydroxymethylmorpholine p-nitrobenzoate showing characteristic peaks at diffraction angles 2θ of about 16.78°, 22.03°, 23.53°, 24.79°, 25.59° and 28.79° (each ±0.2°) in powder X-ray diffraction spectrum.

[21] A crystal of optically active 2-hydroxymethylmorpholine oxalate (preferably, optically active 2-hydroxymethylmorpholine monooxalate) showing characteristic peaks at diffraction angles 2θ of about 20.97°, 21.93°, 25.14°, 26.48° and 34.73° (each ±0.2°) in powder X-ray diffraction spectrum.

[22] A crystal of optically active 2-hydroxymethylmorpholine fumarate (preferably, optically active 2-hydroxymethylmorpholine monofumarate) showing characteristic peaks at diffraction angles 2θ of about 12.20°, 18.88°, 20.09°, 23.49° and 25.23° (each ±0.2°) in powder X-ray diffraction spectrum.

[23] A crystal of optically active 2-hydroxymethylmorpholine maleate (preferably, optically active 2-hydroxymethylmorpholine monomaleate) showing characteristic peaks at diffraction angles 2θ of about 13.08°, 19.93°, 23.44°, 33.88° and 48.37° (each ±0.2°) in powder X-ray diffraction spectrum.

[24] A crystal of optically active 2-hydroxymethylmorpholine terephthalate (preferably, optically active 2-hydroxymethylmorpholine 0.5 terephthalate) showing characteristic peaks at diffraction angles 2θ of about 15.84°, 18.45°, 20.29°, 22.37° and 29.97° (each ±0.2°) in powder X-ray diffraction spectrum.

Effect of the Invention

The present invention enables convenient removal of impurities such as a 1,4-oxazepane compound and the like from a reaction composition containing 2-hydroxymethylmorpholine and the 1,4-oxazepane compound in a short step without using a special low temperature facility, and can produce a 2-hydroxymethylmorpholine salt having high purity.

The thus-obtained 2-hydroxymethylmorpholine salt is a stable and easily handleable solid, and useful as an industrial product.

DESCRIPTION OF EMBODIMENTS

The present invention is explained in detail in the following.

In the present invention, a 2-hydroxymethylmorpholine salt with high purity can be conveniently produced by crystallization from a solution containing 2-hydroxymethylmorpholine represented by the following formula (1)

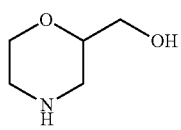 (1)

(hereinafter to be referred to as 2-hydroxymethylmorpholine (1)), a 1,4-oxazepane compound represented by the following formula (2)

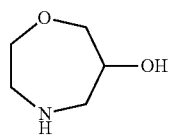
(2)

(hereinafter to be referred to as 1,4-oxazepane compound (2)), and an acid.

The solution to be used in the present invention contains at least 2-hydroxymethylmorpholine (1) and 1,4-oxazepane compound (2). While the ratio thereof is not particularly limited, for example, the ratio (2-hydroxymethylmorpholine (1):1,4-oxazepane compound (2)) is within the range of 99:1 to 20:80.

While the preparation method of the solution containing 2-hydroxymethylmorpholine (1), 1,4-oxazepane compound (2) and an acid to be used in the present invention is not particularly limited, a preferable embodiment is, for example, a method of mixing a composition containing 2-hydroxymethylmorpholine (1) and 1,4-oxazepane compound (2) with an acid.

While the synthesis method of the composition containing 2-hydroxymethylmorpholine (1) and 1,4-oxazepane compound (2) is not particularly limited, for example, the following synthesis method can be mentioned.

That is, an epihalohydrin represented by the following formula (4)

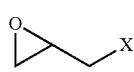
(4)

wherein X is a chlorine atom or a bromine atom (hereinafter to be referred to as epihalohydrin (4)) is reacted with an N-protected ethanolamine represented by the formula (5)

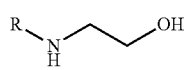
(5)

wherein R is a protecting group selected from a $C_{1-6}$ alkyl group, an allyl group and a benzyl group (hereinafter to be referred to as N-protected ethanolamine (5)) to give a reaction composition containing an N-protected 2-hydroxymethylmorpholine represented by the following formula (8)

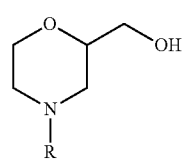
(8)

wherein R is as defined above (hereinafter to be referred to as N-protected 2-hydroxymethylmorpholine (8)), and an N-protected 1,4-oxazepane compound represented by the following formula (9)

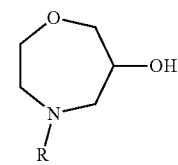
(9)

wherein R is as defined above (hereinafter to be referred to as N-protected 1,4-oxazepane compound (9)), and then R is removed, whereby a composition containing 2-hydroxymethylmorpholine (1) and 1,4-oxazepane compound (2) can be synthesized.

Here, examples of the $C_{1-6}$ alkyl group for R include a methyl group, an ethyl group, an n-propyl group, an isopropyl group, a butyl group, an isobutyl group, a sec-butyl group, a tert-butyl group, a pentyl group, a hexyl group and the like. Preferred are a methyl group, an ethyl group and a propyl group, and more preferred is a methyl group.

While the reaction of epihalohydrin (4) and N-protected ethanolamine (5) is not particularly limited, preferably, epihalohydrin (4) is added to N-protected ethanolamine (5) in a solvent to produce an addition compound represented by the following formula (6)

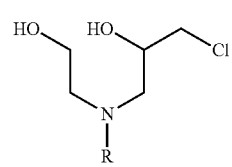
(6)

wherein R is as defined above (hereinafter to be referred to as addition compound (6)) as an intermediate, and then alkali is added to allow reaction to give a composition containing N-protected 2-hydroxymethylmorpholine (8) and N-protected 1,4-oxazepane compound (9), via an epoxy compound represented by the formula (7)

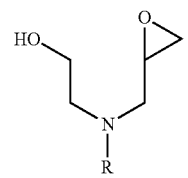
(7)

wherein R is as defined above.

Examples of the solvent to be used in the above-mentioned reaction include water; alcohol solvents such as methanol, ethanol, n-propanol, isopropanol and the like, ether solvents such as tetrahydrofuran, diethyl ether, methyl-t-butylether and the like, aromatic hydrocarbon solvents such as benzene, toluene and the like, aliphatic hydrocarbon solvents such as pentane, hexane, heptane, cyclohexane and the like, halogen solvents such as methylene chloride, 1,2-dichloroethane and the like, ester solvents such as methyl acetate, ethyl acetate and the like, ketone solvents such as acetone, methyl ethyl ketone, methyl isobutyl ketone and the like, nitrile solvents such as acetonitrile, propionitrile and the like, and a mixed solvent thereof. When a mixed solvent is used, the mixing ratio is not particularly limited. The amount of the solvent to be used is 0.5- to 4-fold (v/w) relative to N-protected ethanolamine (5).

The amount of epihalohydrin (4) to be used is 0.5 to 2 equivalents, preferably 0.9 to 1.1 equivalents, relative to N-protected ethanolamine (5).

For producing addition compound (6), the reaction temperature is 0 to 60° C., and the reaction time is 1 to 48 hr.

Examples of the alkali include alkali metal hydroxides such as sodium hydroxide, potassium hydroxide and the like, alkali metal carbonates such as sodium carbonate, potassium carbonate and the like, alkali metal hydrogen carbonates such as sodium hydrogen carbonate, potassium hydrogen carbonate and the like, and the like, which are preferably used as an aqueous solution. The amount of the alkali to be used is 1 to 3 equivalents relative to N-protected ethanolamine (5).

For producing a mixture of N-protected 2-hydroxymethylmorpholine (8) and N-protected 1,4-oxazepane compound (9), the reaction temperature is 0 to 60° C., and the reaction time is 1 to 48 hr.

After the completion of the reaction, the solvent is evaporated as necessary, and the residue is extracted with toluene, ethyl acetate and the like, and the organic layer is washed with water and concentrated to give a crude reaction composition containing N-protected 2-hydroxymethylmorpholine (8) and N-protected 1,4-oxazepane compound (9). The obtained crude reaction composition can be purified by a conventional method such as distillation, chromatography and the like, or subjected to the next deprotection step without purification.

The deprotection of the composition by removing R from N-protected 2-hydroxymethylmorpholine (8) and N-protected 1,4-oxazepane compound (9) can be performed by a known method (e.g., the method described in Theodora W. Greene, Greene's Protective Groups in Organic Synthesis, 4th Edition, 2007) according to the kind of R.

For example, the removal of R when it is a $C_{1-6}$ alkyl group can be performed by, for example, the method described in J. Org. Chem. 49, 2795, (1984). That is, a composition containing N-protected 2-hydroxymethylmorpholine (8) and N-protected 1,4-oxazepane compound (9) is reacted with α-chloroethyl chloroformate to give a corresponding α-chloroethylcarbamate, which is hydrolyzed by treating with methanol to remove the alkyl group.

The removal of R when it is an allyl group can be performed by, for example, the method described in Tetrahedron Lett., 22, 1483 (1981). That is, the allyl group can be removed by reaction with a transition metal catalyst such as tetrakis (triphenylphosphine)palladium, tris(triphenylphosphine) rhodium (I) chloride and the like for isomerization to a corresponding enamine, and hydrolyzing the enamine.

The removal of R when it is a benzyl group can be performed by, for example, a general hydrogenation reaction. That is, a benzyl group can be removed by reaction in a solvent such as methanol, ethanol and the like in the presence of a catalyst such as palladium carbon and the like under a hydrogen atmosphere at 10 to 60° C. for 1 to 72 hr.

The thus-obtained crude reaction composition containing 2-hydroxymethylmorpholine (1) and 1,4-oxazepane compound (2) can be purified by a conventional method such as distillation, chromatography and the like, or can be used without purification.

While the acid to be used in the present invention is not particularly limited as long as it forms a salt with 2-hydroxymethylmorpholine (1), specific examples include inorganic acids such as hydrogen fluoride, hydrogen chloride, hydrogen bromide, hydrogen iodide, sulfuric acid, nitric acid and the like, carboxylic acids such as formic acid, acetic acid, propionic acid, butyric acid, pivalic acid, chloroacetic acid, trichloroacetic acid, trifluoroacetic acid, oxalic acid, benzoic acid, p-nitrobenzoic acid, fumaric acid, maleic acid, terephthalic acid and the like, sulfonic acids such as methanesulfonic acid, trifluoromethanesulfonic acid, benzenesulfonic acid, p-toluenesulfonic acid, camphorsulfonic acid and the like. Preferred are hydrogen bromide, sulfuric acid, pivalic acid, oxalic acid, benzoic acid, p-nitrobenzoic acid, fumaric acid, maleic acid, terephthalic acid, methanesulfonic acid, p-toluenesulfonic acid and trifluoroacetic acid, and more preferred are p-nitrobenzoic acid, oxalic acid, fumaric acid, maleic acid, terephthalic acid and trifluoroacetic acid.

While the amount of the aforementioned acid to be used is not particularly limited, an amount capable of forming a salt with 2-hydroxymethylmorpholine (1) and allowing precipitation as crystals may be used. To afford a superior purification effect in a high yield, it is preferably 0.5 to 2 equivalents, more preferably 0.5 to 1.5 equivalents, relative to the total mols of 2-hydroxymethylmorpholine (1) and 1,4-oxazepane compound (2).

When the crude reaction composition of 2-hydroxymethylmorpholine (1) and 1,4-oxazepane compound (2) is to be used without purification, the amount of N-protected ethanolamine (5) used as a starting material is taken as the total mols of 2-hydroxymethylmorpholine (1) and 1,4-oxazepane compound (2), and the acid may be used within the above-mentioned range.

When a composition containing 2-hydroxymethylmorpholine (1) and 1,4-oxazepane compound (2) is to be mixed with an acid, water or an organic solvent may be used. Examples of the organic solvent include alcohol solvents such as methanol, ethanol, n-propanol, isopropanol and the like, ether solvents such as tetrahydrofuran, diethyl ether, methyl-t-butylether and the like, aromatic hydrocarbon solvents such as benzene, toluene and the like, aliphatic hydrocarbon solvents such as pentane, hexane, heptane, cyclohexane and the like, halogen solvents such as methylene chloride, 1,2-dichloroethane and the like, ester solvents such as methyl acetate, ethyl acetate and the like, ketone solvents such as acetone, methyl ethyl ketone, methyl isobutyl ketone and the like, nitrile solvents such as acetonitrile, propionitrile and the like. Preferred are alcohol solvents such as methanol, ethanol, n-propanol, isopropanol and the like, ether solvents such as tetrahydrofuran, diethyl ether, methyl-t-butylether and the like, ketone solvents such as acetone, methyl ethyl ketone, methyl isobutyl ketone and the like, ester solvents such as methyl acetate, ethyl acetate and the like, and more preferred are alcohol solvents such as methanol, ethanol, n-propanol, isopropanol and the like. Water and these organic solvents may be used alone or used in combination of two or more kinds thereof. When two or more kinds are used in combination, the mixing ratio is not particularly limited.

In such solvent, a composition containing 2-hydroxymethylmorpholine (1) and 1,4-oxazepane compound (2) may be mixed with an acid and, where necessary, the mixture may be stirred at −10 to 60° C. for 0.5 to 24 hr.

When the solvent is the same as the solvent to be used for the crystallization to follow next, a 2-hydroxymethylmorpholine salt can be directly crystallized. When the solvent is different from the crystallization solvent, the solvent may be evaporated entirely or partly and other solvent is added.

While the solvent to be used for crystallization is not particularly limited, water and an organic solvent can be used. Examples of the organic solvent include alcohol solvents such as methanol, ethanol, n-propanol, isopropanol and the like, ether solvents such as tetrahydrofuran, diethyl ether, methyl-t-butylether and the like, aromatic hydrocarbon solvents such as benzene, toluene and the like, aliphatic hydrocarbon solvents such as pentane, hexane, heptane, cyclohexane and the like, halogen solvents such as methylene chloride, 1,2-dichloroethane and the like, ester solvents such as methyl acetate, ethyl acetate and the like, ketone solvents such as acetone, methyl ethyl ketone, methyl isobutyl ketone and the like, and nitrile solvents such as acetonitrile, propionitrile and the like. Preferred are alcohol solvents such as methanol, ethanol, n-propanol, isopropanol and the like, ether solvents such as tetrahydrofuran, diethyl ether, methyl-t-butylether and the like, ketone solvents such as acetone, methyl ethyl ketone, methyl isobutyl ketone and the like, ester solvents such as methyl acetate, ethyl acetate and the like, and more preferred are isopropanol and ethyl acetate, and a mixed solvent thereof. Water and these organic solvents may be used alone or used in combination of two or more kinds thereof. When two or more kinds are used in combination, the mixing ratio is not particularly limited as long as it does not influence the formation of a salt of 2-hydroxymethylmorpholine. In addition, the kind, amount of use and mixing ratio of these solvents may be appropriately selected according to the solubility of the salt to be obtained.

As a crystallization method, methods generally used for crystallization of organic substances are used. Examples of the crystallization method include a method of cooling a solution, a method of stirring or standing still a solution, a method of adding a solvent having a comparatively low solubility of a 2-hydroxymethylmorpholine salt, a method of evaporating a part of the solvent, a method of adding a seed crystal to start crystallization, and a combination of these methods.

The crystallization temperature is not particularly limited in the present invention, and is appropriately determined according to the kind of the salt to be crystallized and the kind of the solvent to be used. It is preferably lower than the temperature at which a 2-hydroxymethylmorpholine salt is dissolved in the solvent species or mixed solvent species to be used, and is determined according to the desired precipitation amount and crystal quality, more preferably −10° C. to 60° C.

A 2-hydroxymethylmorpholine salt obtained by crystallization can be collected by a conventional method such as filtration and the like. Where necessary, it may be washed with an organic solvent. It can also be further purified as necessary by means of recrystallization and the like.

In another preferable embodiment using the above-mentioned method, an acid is added for the deprotection of the composition by removing R from N-protected 2-hydroxymethylmorpholine (8) and N-protected 1,4-oxazepane compound (9) to give a reaction composition containing 2-hydroxymethylmorpholine (1), 1,4-oxazepane compound (2) and the acid, followed by crystallization.

While the amount of the acid to be used in this case is not particularly limited, an amount capable of forming a salt with 2-hydroxymethylmorpholine (1) and allowing precipitation as crystals may be used. To afford a superior purification effect in a high yield, it is preferably 0.5 to 2 equivalents, more preferably 0.5 to 1.5 equivalents, relative to the total mols of N-protected 2-hydroxymethylmorpholine (8) and N-protected 1,4-oxazepane compound (9).

When the crude reaction composition of N-protected 2-hydroxymethylmorpholine (8) and N-protected 1,4-oxazepane compound (9) is to be used without purification, the amount of N-protected ethanolamine (5) used as a starting material is taken as the total mols of N-protected 2-hydroxymethylmorpholine (8) and N-protected 1,4-oxazepane compound (9), and the acid may be used within the above-mentioned range.

The conditions for the removal of R in the presence of an acid, and subsequent crystallization conditions (solvent, temperature etc.) are the same as those mentioned above.

Epihalohydrin (4) and N-protected ethanolamine (5) to be used as the starting materials of the above-mentioned method can be produced by a known method, and commercially available products may also be used.

In the production method of the present invention, a solution containing optically active 2-hydroxymethylmorpholine (1), optically active 1,4-oxazepane compound (2) and an acid can also be used. In this case, an optically active 2-hydroxymethylmorpholine salt can be obtained. Being optically active here means that one of the two enantiomers is contained in excess than the other even in a trace level.

Using optically active epihalohydrin (4), which is a commercially available product, as a starting material in the above-mentioned method, a solution containing optically active 2-hydroxymethylmorpholine (1), optically active 1,4-oxazepane compound (2) and an acid can be obtained.

The 2-hydroxymethylmorpholine salt obtained by the method of the present invention is an acid addition salt of 2-hydroxymethylmorpholine and an acid to be used in the method of the present invention, and can be obtained as a stable solid. Therefore, it can be handled easily and distributed preferably as an industrial product. The 2-hydroxymethylmorpholine salt of the present invention may be a crystal or an amorphous form as long as it is a solid, and is preferably a crystal. In addition, it may be a hydrate or solvate.

Moreover, the optically active 2-hydroxymethylmorpholine salt is a novel substance, which is useful as an easily handleable intermediate for pharmaceutical products and the like.

When the acid to be used in the present invention is a monobasic acid or a bibasic acid, the 2-hydroxymethylmorpholine salt can be represented by the following formula (3)

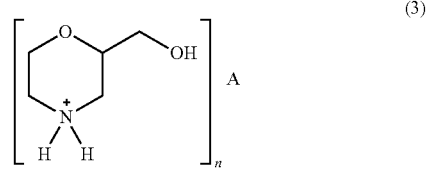

(3)

wherein each symbol is as defined above.

The counter anion for A in the formula is not particularly limited as long as it forms a salt with 2-hydroxymethylmorpholine. Specific examples thereof include fluoride ion (n is 1), chloride ion (n is 1), bromide ion (n is 1), iodide ion (n is 1), sulfuric anion (n is 1 or 2), nitric anion (n is 1), formic anion (n is 1), acetic anion (n is 1), propionic anion (n is 1), butyric anion (n is 1), pivalic anion (n is 1), chloroacetic anion (n is 1), trichloroacetic anion (n is 1), trifluoroacetic ion (n is 1), oxalic anion (n is 1 or 2), benzoic anion (n is 1), p-nitrobenzoic anion (n is 1), fumaric anion (n is 1 or 2), maleic anion (n is 1 or 2), terephthalic anion (n is 1 or 2), methanesulfonic anion (n is 1), trifluoromethanesulfonic anion (n is 1), benzenesulfonic anion (n is 1), p-toluenesulfonic anion (n is 1) and camphorsulfonic anion (n is 1). Preferred are bromide ion (n is 1), sulfuric anion (n is 1 or 2), pivalic anion (n is 1), oxalic anion (n is 1 or 2), benzoic anion (n is 1), p-nitrobenzoic anion (n is 1), fumaric anion (n is 1 or 2), maleic anion (n is 1 or 2), terephthalic anion (n is 1 or 2), methanesulfonic anion (n is 1), p-toluenesulfonic anion (n is 1) and trifluoroacetic anion (n is 1), and more preferred are oxalic anion (n is 1 or 2), p-nitrobenzoic anion (n is 1), fumaric anion (n is 1 or 2), maleic anion (n is 1 or 2), terephthalic anion (n is 1 or 2) and trifluoroacetic anion (n is 1).

In the preferable embodiments of the 2-hydroxymethylmorpholine salt of the present invention, the following salts are obtained as crystals and show the following property values.

Note that (±0.2°) of diffraction angle 2θ in the powder X-ray diffraction spectrum and (±1° C.) of extrapolation melting onset temperature (Tim) and melting peak temperature (Tpm) in the thermogravimetry/differential thermal analysis (TG/DTA) show measurement errors unavoidable from the nature of the measurements, and mean that an error within this range is tolerable.

(1) Optically Active 2-hydroxymethylmorpholine trifluoroacetate (n is 1)

It shows peaks at diffraction angles 2θ of about 9.38°, 15.93°, 17.37°, 18.86°, 19.79°, 20.48°, 21.34°, 22.42°, 25.94°, 28.47° and 29.61° (each ±0.2°), and particularly characteristic peaks at 15.93°, 18.86°, 20.48°, 21.34°, 28.47° and 29.61° (each ±0.2°), in powder X-ray diffraction spectrum.

In thermogravimetry/differential thermal analysis (TG/DTA), it shows a melting peak with extrapolation melting onset temperature (Tim) of about 83° C. (±1° C.) and melting peak temperature (Tpm) of about 91° C. (±1° C.).

(2) Optically Active 2-hydroxymethylmorpholine p-nitrobenzoate (n is 1)

It shows peaks at diffraction angles 2θ of about 10.68°, 13.15°, 14.62°, 16.78°, 17.97°, 19.79°, 22.03°, 23.53°, 24.79°, 25.59°, 27.00° and 28.79° (each ±0.2°), and particularly characteristic peaks at 16.78°, 22.03°, 23.53°, 24.79°, 25.59° and 28.79° (each ±0.2°), in powder X-ray diffraction spectrum.

In thermogravimetry/differential thermal analysis (TG/DTA), it shows a melting peak with extrapolation melting onset temperature (Tim) of about 142° C. (±1° C.) and melting peak temperature (Tpm) of about 153° C. (±1° C.).

(3) Optically Active 2-hydroxymethylmorpholine oxalate (n is 1)

It shows peaks at diffraction angles 2θ of about 12.94°, 17.04°, 18.77°, 20.97°, 21.93°, 23.95°, 25.14°, 26.48°, 34.73° and 36.65° (each ±0.2°), and particularly characteristic peaks at 20.97°, 21.93°, 25.14°, 26.48° and 34.73° (each ±0.2°), in powder X-ray diffraction spectrum.

In thermogravimetry/differential thermal analysis (TG/DTA), it shows a melting peak with extrapolation melting onset temperature (Tim) of about 91° C. (±1° C.) and melting peak temperature (Tpm) of about 100° C. (±1° C.)

(4) Optically Active 2-hydroxymethylmorpholine fumarate (n is 1)

It shows peaks at diffraction angles 2θ of about 12.20°, 18.28°, 18.88°, 20.09°, 23.49°, 25.23°, 27.78°, 34.71° and 35.90° (each ±0.2°), and particularly characteristic peaks at 12.20°, 18.88°, 20.09°, 23.49° and 25.23° (each ±0.2°), in powder X-ray diffraction spectrum.

In thermogravimetry/differential thermal analysis (TG/DTA), it shows a melting peak with extrapolation melting onset temperature (Tim) of about 143° C. (±1° C.) and melting peak temperature (Tpm) of about 152° C. (±1° C.)

(5) Optically Active 2-hydroxymethylmorpholine maleate (n is 1)

It shows peaks at diffraction angles 2θ of about 13.08°, 18.71°, 19.93°, 23.44°, 29.67°, 33.88°, 36.20°, 41.03°, 43.03°, 48.37 and 55.92° (each ±0.2°), and particularly characteristic peaks at 13.08°, 19.93°, 23.44°, 33.88° and 48.37° (each ±0.2°), in powder X-ray diffraction spectrum.

In thermogravimetry/differential thermal analysis (TG/DTA), it shows a melting peak with extrapolation melting onset temperature (Tim) of about 122° C. (±1° C.) and melting peak temperature (Tpm) of about 131° C. (±1° C.).

(6) Optically Active 2-hydroxymethylmorpholine terephthalate (n is 2)

It shows peaks at diffraction angles 2θ of about 9.40°, 15.84°, 16.70°, 18.45°, 20.29°, 22.37°, 24.54°, 29.97°, 38.04° and 43.55° (each ±0.2°), and particularly characteristic peaks at 15.84°, 18.45°, 20.29°, 22.37° and 29.97° (each ±0.2°), in powder X-ray diffraction spectrum.

In thermogravimetry/differential thermal analysis (TG/DTA), it shows a melting peak with extrapolation melting onset temperature (Tim) of about 148° C. (±1° C.) and melting peak temperature (Tpm) of about 157° C. (±1° C.)

EXAMPLES

The present invention is explained by referring to the following Examples, which are not to be construed as limitative.

(Measurement Method of Optical Purity of 2-hydroxymethylmorpholine salt)

In the below-mentioned Examples, a 2-hydroxymethylmorpholine salt was analyzed by the HPLC analysis method shown below.

To a solution of isopropanol (1 mL), triethylamine (131 mg, 1.29 mmol), and di t-butyl dicarbonate (193 mg, 0.88 mmol) was added a 2-hydroxymethylmorpholine salt (200 mg), and the mixture was stirred at room temperature for 1 hr. Water (2 mL) and ethyl acetate (7 mL) were added, and the aqueous layer was separated. The organic layer was washed with water (2 mL), and dried over magnesiumسulfate. The organic layer was filtered, and the filtrate was concentrated under reduced pressure. The residue was dissolved in isopropanol/hexane=1/9 (v/v) solution (5 mL) and used as a sample solution to be subjected to HPLC analysis at an injection volume of 5 μL.

<HPLC Conditions> column: DAICEL CHIRALPAK AD-H 4.6×250 mm
eluent: isopropanol/hexane=5/95 (v/v)
flow rate: 1 mL/min.
column temperature: 25° C.
detector: UV 215 nm
R form retention time=14.0 min, S form retention time=17.6 min (Measurement Method of Powder X-Ray Diffraction Spectrum of 2-hydroxymethylmorpholine salt)

In the below-mentioned Examples, powder X-ray diffraction spectrum of 2-hydroxymethylmorpholine salt was measured under the following conditions.

apparatus: RAD-rX (Rigaku Corporation)
X-ray: Cu K-ALPHA/40 kV/100 mA
goniometer: wide-angle goniometer
attachment: standard sample holder
filter: Kβ filter
counter monochromator: not used
divergence slit: 1 deg/scattering slit: 1 deg/receiving slit: 0.15 mm
scanning mode: continuous
scanning speed: 3°/min
sampling width: 0.01°
scan axis: 2θ/θ
scanning range: 3-90°
cumulated number: 1

(Measurement Method of Thermogravimetry/Differential Thermal Analysis (TG/DTA) of 2-hydroxymethylmorpholine salt)

In the below-mentioned Examples, the thermogravimetry/differential thermal analysis (TG/DTA) spectrum of a 2-hydroxymethylmorpholine salt was measured under the following conditions.

apparatus: TG/DTA6300 (manufactured by Seiko Instruments Inc.)
sampling amount: 5 to 6 mg
sample cell: aluminum cell
nitrogen gas flow: 100 ml/min
temperature rise rate: 10° C./min Production Example 1

Production of seed crystal of (R)-2-hydroxymethylmorpholine trifluoroacetate

To a mixture of N-benzylethanolamine (81.7 g, 0.540 mol), 2-propanol (50 ml) and water (50 ml) was added dropwise at 15 to 25° C. (S)-epichlorohydrin (50.0 g, 0.540 mol, 99% ee). After reaction at 15 to 25° C. for 7 hr, aqueous 24% NaOH solution (NET 28.1 g, 0.703 mol) was added at 5 to 10° C. After reaction at 25° C. for 20 hr, the reaction mixture was concentrated under reduced pressure to evaporate 2-propanol. To the residue was added toluene (150 ml) and, after partitioning, the organic layer was concentrated under reduced pressure. The residue was distilled (0.5 mmHg, 150 to 180° C.) to give a mixture of N-benzyl-2-hydroxymethylmorpholine and N-benzyl-1,4-oxazepane compound (about 70 g, N-benzyl-2-hydroxymethylmorpholine:N-benzyl-1,4-oxazepane compound=76:24). To this mixture (50.0 g) were added methanol (150 ml), trifluoroacetic acid (27.5 g, 0.241 mol) and palladium carbon (10.0 g when dry), and the mixture was reacted under hydrogen stream at 25° C. for 15 hr. Palladium carbon was filtered off, and the filtrate was concentrated under reduced pressure. The residue was subjected twice to azeotropic distillation with dehydrating with 2-propanol (50 ml). To the residue after azeotropic distillation with dehydrating was added ethyl acetate (150 ml) at 40° C., and the mixture was cooled to 10° C. After crystallization, the mixture was further stirred for 1 hr. The crystal was collected by filtration, washed twice with ethyl acetate (76 ml) and dried (1 mmHg, 40° C.) to give (R)-2-hydroxymethylmorpholine trifluoroacetate as crystals (about 20 to 25 g). The obtained crystals were used as a seed crystal in the following Examples.

Example 1

Production of (R)-2-hydroxymethylmorpholine trifluoroacetate

To a mixture of N-benzylethanolamine (40.9 g, 0.270 mol), 2-propanol (25 ml) and water (25 ml) was added dropwise at 15 to 25° C. (S)-epichlorohydrin (25.0 g, 0.270 mol, 99% ee). After reaction at 15 to 25° C. for 7 hr, aqueous 24% NaOH solution (NET 14.05 g, 0.351 mol) was added at 5 to 10° C. After reaction at 25° C. for 20 hr, the reaction mixture was concentrated under reduced pressure to evaporate 2-propanol. To the residue was added toluene (75 ml) and, after partitioning, the organic layer was concentrated under reduced pressure. To the obtained residue (53.9 g) were added methanol (161.8 ml) and palladium carbon (18.9 g when dry), and the mixture was reacted under a hydrogen stream at 40° C. for 30 hr. Palladium carbon was filtered off, and the filtrate was concentrated under reduced pressure and the residue was distilled (0.5 mmHg, 115 to 135° C.) to give a mixture of 2-hydroxymethylmorpholine and 1,4-oxazepane compound (21.6 g, 2-hydroxymethylmorpholine: 1,4-oxazepane compound=79.0:21.0). To this mixture was added methanol (22 ml), and trifluoroacetic acid (22.1 g, 0.194 mol) was added dropwise at 0 to 25° C. After stirring at 25° C. for 1 hr, the mixture was concentrated under reduced pressure. To the residue was added ethyl acetate (108 ml) at 40° C., and the mixture was cooled to 20° C. Seed crystal was added and, after crystallization, the mixture was cooled to 0° C. and stirred for 1 hr. The crystals were collected by filtration, washed withed twice with ethyl acetate (22 ml) and dried (1 mmHg, 40° C.) to give (R)-2-hydroxymethylmorpholine trifluoroacetate (26.49 g) (yield from (S)-epichlorohydrin 42.4%). The obtained (R)-2-hydroxymethylmorpholine trifluoroacetate was analyzed by HPLC to find an optical purity of 99% ee.

The obtained (R)-2-hydroxymethylmorpholine trifluoroacetate was measured for powder X-ray diffraction spectrum and thermogravimetry/differential thermal analysis (TG/DTA) spectrum and showed the following property values.

It showed peaks at diffraction angles 2θ of about 9.38°, 15.93°, 17.37°, 18.86°, 19.79°, 20.48°, 21.34°, 22.42°, 22.94°, 28.47° and 29.61° (each ±0.2°), and particularly characteristic peaks at 15.93°, 18.86°, 20.48°, 21.34°, 28.47° and 29.61° (each ±0.2°), in powder X-ray diffraction spectrum.

In thermogravimetry/differential thermal analysis (TG/DTA), it shows a single melting peak with extrapolation melting onset temperature (Tim) of about 83° C. (±1° C.) and melting peak temperature (Tpm) of about 91° C. (±1° C.).

Example 2

Production of (R)-2-hydroxymethylmorpholine trifluoroacetate

To a mixture of N-benzylethanolamine (81.7 g, 0.540 mol), 2-propanol (50 ml) and water (50 ml) was added dropwise at 15 to 25° C. (S)-epichlorohydrin (50.0 g, 0.540 mol, 99% ee). After reaction at 10 to 25° C. for 7 hr, aqueous 24% NaOH solution (NET 28.1 g, 0.703 mol) was added at 5 to 10° C. After reaction at 25° C. for 20 hr, the reaction mixture was concentrated under reduced pressure to evaporate 2-propanol. To the residue was added toluene (150 ml) and, after partitioning, the organic layer was concentrated under reduced pressure. The residue was distilled (0.5 mmHg, 150 to 180° C.) to give a mixture of N-benzyl-2-hydroxymethylmorpholine and N-benzyl-1,4-oxazepane compound (76.3 g, N-benzyl-2-hydroxymethylmorpholine:N-benzyl-1,4-oxazepane compound=76.5:23.5). To this mixture were added methanol (153 ml), trifluoroacetic acid (44.1 g, 0.387 mol) and palladium carbon (15.3 g when dry), and the mixture was reacted under a hydrogen stream at 25° C. for 15 hr. Palladium carbon was filtered off, and the filtrate was concentrated under reduced pressure. The residue was subjected twice to azeotropic distillation with dehydrating with 2-propanol (76 ml). To the residue after azeotropic distillation with dehydrating was added ethyl acetate (382 ml) at 40° C., and the mixture was cooled to 20° C. Seed crystal was added and, after crystallization, the mixture was cooled to 0° C. and stirred for 1 hr. The crystals were collected by filtration, washed withed twice with ethyl acetate (76 ml) and dried (1 mmHg, 40° C.) to give (R)-2-hydroxymethylmorpholine trifluoroacetate (50.22 g) (yield from (S)-epichlorohydrin:

40.2%). The obtained (R)-2-hydroxymethylmorpholine trifluoroacetate was analyzed by HPLC to find an optical purity of 99% ee.

Example 3

Production of (R)-2-hydroxymethylmorpholine trifluoroacetate

To a mixture of N-benzylethanolamine (81.7 g, 0.540 mol), 2-propanol (50 ml) and water (50 ml) was added dropwise at 15 to 25° C. (S)-epichlorohydrin (50.0 g, 0.540 mol, 99% ee). After reaction at 10 to 25° C. for 7 hr, aqueous 24% NaOH solution (NET 28.1 g, 0.703 mol) was added at 5 to 10° C. After reaction at 25° C. for 20 hr, the reaction mixture was concentrated under reduced pressure to evaporate 2-propanol. To the residue was added toluene (150 ml) and, after partitioning, the organic layer was concentrated under reduced pressure to give a mixture of N-benzyl-2-hydroxymethylmorpholine and N-benzyl-1,4-oxazepane (125.3 g, N-benzyl-2-hydroxymethylmorpholine:N-benzyl-1,4-oxazepane compound=74.4:25.6). To this mixture were added methanol (200 ml) and palladium carbon (11.0 g when dry), and the mixture was reacted under a hydrogen stream at 25° C. for 15 hr. Palladium carbon was filtered off, trifluoroacetic acid (61.8 g, 0.540 mol) was added to the filtrate at 5 to 10° C., and methanol was evaporated under reduced pressure. The residue was subjected twice to azeotropic distillation with dehydrating with 2-propanol (100 ml). To the residue after azeotropic distillation with dehydrating was added ethyl acetate (450 ml) at 40° C., and the mixture was cooled to 20° C. Seed crystal was added and, after crystallization, the mixture was cooled to 0° C. and stirred for 1 hr. The crystals were collected by filtration, washed withed twice with ethyl acetate (100 ml) and dried (1 mmHg, 40° C.) to give (R)-2-hydroxymethylmorpholine trifluoroacetate (51.3 g) (yield from (S)-epichlorohydrin 41.1%). The obtained (R)-2-hydroxymethylmorpholine trifluoroacetate was analyzed by HPLC to find an optical purity of 99% ee.

Example 4

Production of (R)-2-hydroxymethylmorpholine trifluoroacetate

In the same manner as in Example 3, a mixture containing N-benzyl-2-hydroxymethylmorpholine, N-benzyl-1,4-oxazepane and other byproducts (121.1 g, N-benzyl-2-hydroxymethylmorpholine:N-benzyl-1,4-oxazepane compound=75.1:24.9). To this mixture were added methanol (200 ml), trifluoroacetic acid (61.8 g, 0.540 mol), and palladium carbon (11.0 g when dry), and the mixture was reacted under a hydrogen stream at 25° C. for 15 hr. Palladium carbon was filtered off, and methanol was evaporated under reduced pressure. The residue was subjected twice to azeotropic distillation with dehydrating with 2-propanol (100 ml). To the residue after azeotropic distillation with dehydrating was added ethyl acetate (450 ml) at 40° C., and the mixture was cooled to 20° C. Seed crystal was added and, after crystallization, the mixture was cooled to 0° C. and stirred for 1 hr. The crystals were collected by filtration, washed withed twice with ethyl acetate (100 ml) and dried (1 mmHg, 40° C.) to give (R)-2-hydroxymethylmorpholine trifluoroacetate (53.7 g) (yield from (S)-epichlorohydrin: 43.0%). The obtained (R)-2-hydroxymethylmorpholine trifluoroacetate was analyzed by HPLC to find an optical purity of 99% ee.

Example 5

Production of (R)-2-hydroxymethylmorpholine p-nitrobenzoate

To a mixture of N-benzylethanolamine (302.4 g, 2.0 mol), 2-propanol (185 ml) and water (185 ml) was added dropwise at 15 to 25° C. (S)-epichlorohydrin (185.0 g, 2.0 mol, 99% ee). After reaction at 15 to 25° C. for 7 hr, aqueous 24% NaOH solution (NET 104 g, 2.6 mol) was added at 5 to 10° C. After reaction at 25° C. for 20 hr, the reaction mixture was concentrated under reduced pressure to evaporate 2-propanol. To the residue was added toluene (555 ml) and, after partitioning, the organic layer was concentrated under reduced pressure to give a mixture of N-benzyl-2-hydroxymethylmorpholine, N-benzyl-1,4-oxazepane and other byproducts (410.4 g, N-benzyl-2-hydroxymethylmorpholine:N-benzyl-1,4-oxazepane compound=75.2:24.8). To this mixture were added methanol (830 ml) and palladium carbon (40.0 g when dry), and the mixture was reacted under a hydrogen stream at 25° C. for 15 hr. Palladium carbon was filtered off, methanol was evaporated under reduced pressure to give a mixture of 2-hydroxymethylmorpholine and a 1,4-oxazepane compound (265.7 g, 2-hydroxymethylmorpholine:1,4-oxazepane compound=75.8:24.2). To the mixture (20.0 g) were added methanol (100 ml) and p-nitrobenzoic acid (25.2 g, 0.151 mol) and the mixture was stirred for 30 min. Then, methanol was evaporated under reduced pressure. To the residue was added 2-propanol (50 ml) and the mixture was subjected twice to azeotropic distillation with dehydrating. To the residue after azeotropic distillation with dehydrating was added ethyl acetate (100 ml) at 40° C., and the mixture was cooled to 10° C. After crystallization, the mixture was cooled to 0° C. and stirred for 1 hr. The crystals were collected by filtration, washed withed twice with ethyl acetate (25 ml) and dried (1 mmHg, 40° C.) to give (R)-2-hydroxymethylmorpholine p-nitrobenzoate (17.7 g) (yield from (S)-epichlorohydrin 41.3%). The obtained (R)-2-hydroxymethylmorpholine p-nitrobenzoate was analyzed by HPLC to find an optical purity of 99% ee.

The obtained (R)-2-hydroxymethylmorpholine p-nitrobenzoate was measured for powder X-ray diffraction spectrum and thermogravimetry/differential thermal analysis (TG/DTA) spectrum and showed the following property values.

It showed peaks at diffraction angles 2θ of about 10.68°, 13.15°, 14.62°, 16.78°, 17.97°, 19.79°, 22.03°, 23.53°, 24.79°, 25.59°, 27.00° and 28.79° (each ±0.2°), and particularly characteristic peaks at 16.78°, 22.03°, 23.53°, 24.79°, 25.59° and 28.79° (each ±0.2°), in powder X-ray diffraction spectrum.

In thermogravimetry/differential thermal analysis (TG/DTA), it shows a single melting peak with extrapolation melting onset temperature (Tim) of about 142° C. (±1° C.) and melting peak temperature (Tpm) of about 153° C. (±1° C.).

Example 6

Production of (R)-2-hydroxymethylmorpholine oxalate

To a mixture of 2-hydroxymethylmorpholine and 1,4-oxazepane compound (20.0 g, 2-hydroxymethylmorpholine:1,4-oxazepane compound=75.8:24.2) synthesized in Example 5 were added methanol (100 ml) and oxalic acid (13.6 g, 0.151 mol) and the mixture was stirred for 30 min. Methanol was evaporated under reduced pressure. To the residue was added 2-propanol (50 ml) and the mixture was subjected twice to azeotropic distillation with dehydrating. To the residue after azeotropic distillation with dehydrating was added ethyl acetate (100 ml) at 40° C., and the mixture was cooled to 10° C. After crystallization, the mixture was cooled to 0° C. and stirred for 1 hr. The crystals were collected by filtration, washed withed twice with ethyl acetate (25 ml) and dried (1 mmHg, 40° C.) to give (R)-2-hydroxymethylmorpholine oxalate (12.6 g) (2-hydroxymethylmorpholine:oxalic acid=1:1, yield from (S)-epichlorohydrin 40.5%). The obtained (R)-2-hydroxymethylmorpholine oxalate was analyzed by HPLC to find an optical purity of 99% ee.

The obtained (R)-2-hydroxymethylmorpholine oxalate was measured for powder X-ray diffraction spectrum and thermogravimetry/differential thermal analysis (TG/DTA) spectrum and showed the following property values.

It showed peaks at diffraction angles 2θ of about 12.94°, 17.04°, 18.77°, 20.97°, 21.93°, 23.95°, 25.14°, 26.48°, 34.73° and 36.65° (each ±0.2°), and particularly characteristic peaks at 20.97°, 21.93°, 25.14°, 26.48° and 34.73° (each ±0.2°), in powder X-ray diffraction spectrum.

In thermogravimetry/differential thermal analysis (TG/DTA), it shows a melting peak with extrapolation melting onset temperature (Tim) of about 91° C. (±1° C.) and melting peak temperature (Tpm) of about 100° C. (±1° C.) as a main peak.

Example 7

Production of (R)-2-hydroxymethylmorpholine fumarate

To a mixture of 2-hydroxymethylmorpholine and 1,4-oxazepane compound (20.0 g, 2-hydroxymethylmorpholine:1,4-oxazepane compound=75.8:24.2) synthesized in Example 5 were added methanol (100 ml) and fumaric acid (17.5 g, 0.151 mol) and the mixture was stirred for 30 min. Methanol was evaporated under reduced pressure. To the residue was added 2-propanol (50 ml) and the mixture was subjected twice to azeotropic distillation with dehydrating. To the residue after azeotropic distillation with dehydrating was added ethyl acetate (100 ml) at 40° C., and the mixture was cooled to 10° C. After crystallization, the mixture was cooled to 0° C. and stirred for 1 hr. The crystals were collected by filtration, washed withed twice with ethyl acetate (25 ml) and dried (1 mmHg, 40° C.) to give (R)-2-hydroxymethylmorpholine fumarate (14.8 g) (2-hydroxymethylmorpholine:fumaric acid=1:1, yield from (S)-epichlorohydrin: 42.2%). The obtained (R)-2-hydroxymethylmorpholine fumarate was analyzed by HPLC to find an optical purity of 99% ee.

The obtained (R)-2-hydroxymethylmorpholine fumarate was measured for powder X-ray diffraction spectrum and thermogravimetry/differential thermal analysis (TG/DTA) spectrum and showed the following property values.

It showed peaks at diffraction angles 2θ of about 12.20°, 18.28°, 18.88°, 20.09°, 23.49°, 25.23°, 27.78°, 34.71° and 35.90° (each ±0.2°), and particularly characteristic peaks at 12.20°, 18.88°, 20.09°, 23.49° and 25.23° (each ±0.2°), in powder X-ray diffraction spectrum.

In thermogravimetry/differential thermal analysis (TG/DTA), it shows a single melting peak with extrapolation melting onset temperature (Tim) of about 143° C. (±1° C.) and melting peak temperature (Tpm) of about 152° C. (±1° C.).

Example 8

Production of (R)-2-hydroxymethylmorpholine maleate

To a mixture of 2-hydroxymethylmorpholine and 1,4-oxazepane compound (20.0 g, 2-hydroxymethylmorpholine:1,4-oxazepane compound=75.8:24.2) synthesized in Example 5 were added methanol (100 ml) and maleic acid (17.5 g, 0.151 mol) and the mixture was stirred for 30 min. Methanol was evaporated under reduced pressure. To the residue was added 2-propanol (50 ml) and the mixture was subjected twice to azeotropic distillation with dehydrating. To the residue after azeotropic distillation with dehydrating was added ethyl acetate (100 ml) at 40° C., and the mixture was cooled to 10° C. After crystallization, the mixture was cooled to 0° C. and stirred for 1 hr. The crystals were collected by filtration, washed withed twice with ethyl acetate (25 ml) and dried (1 mmHg, 40° C.) to give (R)-2-hydroxymethylmorpholine maleate (13.8 g) (2-hydroxymethylmorpholine:maleic acid=1:1, yield from (S)-epichlorohydrin: 39.2%). The obtained (R)-2-hydroxymethylmorpholine maleate was analyzed by HPLC to find an optical purity of 99% ee.

The obtained (R)-2-hydroxymethylmorpholine maleate was measured for powder X-ray diffraction spectrum and thermogravimetry/differential thermal analysis (TG/DTA) spectrum and showed the following property values.

It showed peaks at diffraction angles 2θ of about 13.08°, 18.71°, 19.93°, 23.44°, 29.67°, 33.88°, 36.20°, 41.03°, 43.03°, 48.37 and 55.92° (each ±0.2°), and particularly characteristic peaks at 13.08°, 19.93°, 23.44°, 33.88° and 48.37° (each ±0.2°), in powder X-ray diffraction spectrum.

In thermogravimetry/differential thermal analysis (TG/DTA), it shows a single melting peak with extrapolation melting onset temperature (Tim) of about 122° C. (±1° C.) and melting peak temperature (Tpm) of about 131° C. (±1° C.).

Example 9

Production of (R)-2-hydroxymethylmorpholine terephthalate

To a mixture of 2-hydroxymethylmorpholine and 1,4-oxazepane compound (20.0 g, 2-hydroxymethylmorpholine:1,4-oxazepane compound=75.8:24.2) synthesized in Example 5 were added methanol (100 ml) and terephthalic acid (12.5 g, 0.075 mol) and the mixture was stirred for 30 min. Methanol was evaporated under reduced pressure. To the residue was added 2-propanol (50 ml) and the mixture was subjected twice to azeotropic distillation with dehydrating. To the residue after azeotropic distillation with dehydrating was added ethyl acetate (100 ml) at 40° C., and the mixture was cooled to 10° C. After crystallization, the mixture was cooled to 0° C. and stirred for 1 hr. The crystals were collected by filtration, washed withed twice with ethyl acetate (25 ml) and dried (1 mmHg, 40° C.) to give (R)-2-hydroxymethylmorpholine terephthalate (10.1 g) (2-hydroxymethylmorpholine:terephthalic acid=2:1, yield from (S)-epichlorohydrin: 33.5%). The obtained (R)-2-hydroxymethylmorpholine terephthalate was analyzed by HPLC to find an optical purity of 99% ee.

The obtained (R)-2-hydroxymethylmorpholine terephthalate was measured for powder X-ray diffraction spectrum and thermogravimetry/differential thermal analysis (TG/DTA) spectrum and showed the following property values.

It showed peaks at diffraction angles 2θ of about 9.40°, 15.84°, 16.70°, 18.45°, 20.29°, 22.37°, 24.54°, 29.97°, 38.04° and 43.55° (each ±0.2°), and particularly characteristic peaks at 15.84°, 18.45°, 20.29°, 22.37° and 29.97° (each ±0.2°), in powder X-ray diffraction spectrum.

In thermogravimetry/differential thermal analysis (TG/DTA), it shows a single melting peak with extrapolation melting onset temperature (Tim) of about 148° C. (±1° C.) and melting peak temperature (Tpm) of about 157° C. (±1° C.).

INDUSTRIAL APPLICABILITY

A 2-hydroxymethylmorpholine salt produced by the method of the present invention is useful as an intermediate for pharmaceutical products, agricultural chemicals and the like.

This application is based on a patent application No. 2009-007282 filed in Japan, the contents of which are incorporated in full herein.

Although the present invention have been presented or described by referring to preferred embodiments of this invention, it will, however, be understood by those of ordinary skill in the art that various modifications may be made to the forms and details without departing from the scope of the invention as set forth in the appended claims. All patents, patent publications and other publications indicated or cited in the Specification are hereby incorporated in their entireties by reference.

The invention claimed is:

1. A method of producing a 2-hydroxymethylmorpholine salt of formula (3)

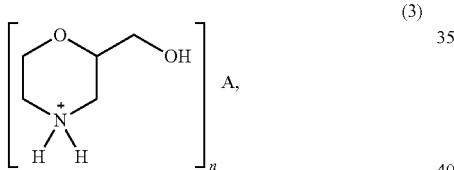

(3)

wherein A is an acidic counter anion, and n is an integer of 1 or 2, comprising crystallizing the salt from a solution containing 2-hydroxymethylmorpholine of formula (1)

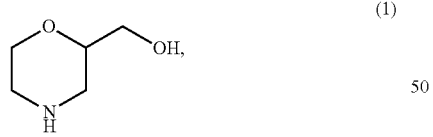

(1)

1,4-oxazepane compound of formula (2)

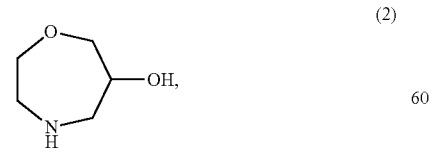

(2)

and an acid selected from an inorganic acid, a carboxylic acid and a sulfonic acid.

2. The production method according to claim 1 comprising mixing a composition containing the 2-hydroxymethylmorpholine of formula (1) and the 1,4-oxazepane compound of formula (2) with an acid to allow crystallization.

3. The production method according to claim 2, wherein the composition containing the 2-hydroxymethylmorpholine of formula (1) and the 1,4-oxazepane compound of formula (2) is obtained by reacting an epihalohydrin of formula (4)

(4)

wherein X is a chlorine atom or a bromine atom, with an N-protected ethanolamine of formula (5)

(5)

wherein R is a protecting group selected from a $C_{1-6}$ alkyl group, an ally group and a benzyl group, to give a reaction composition containing an N-protected 2-hydroxymethylmorpholine of formula (8)

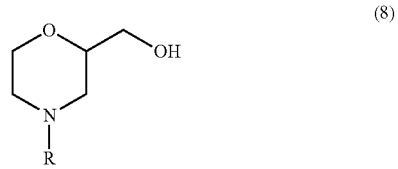

(8)

wherein R is as defined above, and an N-protected 1,4-oxazepane compound of formula (9)

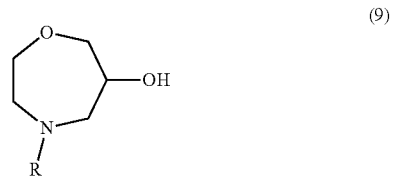

(9)

wherein R is as defined above, and then subjecting the reacting composition to deprotection to remove R.

4. The production method according to claim 1, which comprises a step of subjecting a composition containing an N-protected 2-hydroxymethylmorpholine of formula (8)

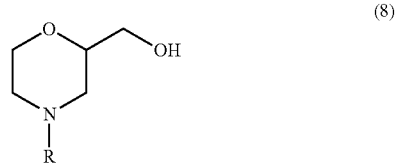

(8)

wherein R is a protecting group selected from a $C_{1-6}$ alkyl group, an allyl group and a benzyl group, and an N-protected 1,4-oxazepane compound of formula (9)

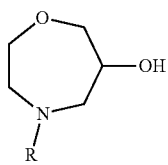

wherein R is as defined above, to deprotection in the presence of an acid to remove R to give a reaction composition containing 2-hydroxymethylmorpholine of formula (1)

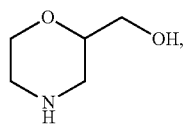

1,4-oxazepane compound of formula (2)

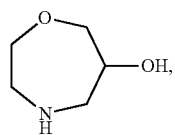

and an acid, and then allowing crystallization.

5. The production method according to claim 4, wherein the composition containing the N-protected 2-hydroxymethylmorpholine of formula (8) and the N-protected 1,4-oxazepane compound of formula (9) is obtained by reacting an epihalohydrin of formula (4)

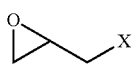

wherein X is a chlorine atom or a bromine atom, with an N-protected ethanolamine of formula (5)

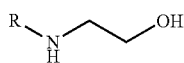

wherein R is a protecting group selected from a $C_{1-6}$ alkyl group, an allyl group and a benzyl group.

6. The production method according to claim 1, wherein the acid is an inorganic acid selected from hydrogen fluoride, hydrogen chloride, hydrogen bromide, hydrogen iodide, sulfuric acid and nitric acid.

7. The production method according to claim 1, wherein the acid is a carboxylic acid selected from formic acid, acetic acid, propionic acid, butyric acid, pivalic acid, chloroacetic acid, trichloroacetic acid, trifluoroacetic acid, oxalic acid, benzoic acid, p-nitrobenzoic acid, fumaric acid, maleic acid and terephthalic acid.

8. The production method according to claim 1, wherein the acid is a sulfonic acid selected from methanesulfonic acid, trifluoromethanesulfonic acid, benzenesulfonic acid, p-toluenesulfonic acid and camphorsulfonic acid.

9. The production method according to claim 1, wherein the salt is crystallized from a solution of at least one kind of solvent selected from water, alcohol solvents, ether solvents, aromatic hydrocarbon solvents, aliphatic hydrocarbon solvents, halogen solvents, ester solvents, ketone solvents and nitrile solvents.

10. The production method according to claim 9, wherein the salt is crystallized from a solution of an ester solvent.

11. The production method according to claim 3, wherein R is a benzyl group.

12. The production method according to claim 1, wherein the 2-hydroxymethylmorpholine salt is an optically active form.

13. The production method according to claim 4, wherein R is a benzyl group.

* * * * *

UNITED STATES PATENT AND TRADEMARK OFFICE
CERTIFICATE OF CORRECTION

| | | |
|---|---|---|
| PATENT NO. | : 8,648,190 B2 | Page 1 of 1 |
| APPLICATION NO. | : 13/144202 | |
| DATED | : February 11, 2014 | |
| INVENTOR(S) | : Nagano et al. | |

It is certified that error appears in the above-identified patent and that said Letters Patent is hereby corrected as shown below:

<u>In the claims</u>

Claim 3, column 22, line 24, "an ally group" should read "an allyl group"

Signed and Sealed this
Seventh Day of October, 2014

Michelle K. Lee
*Deputy Director of the United States Patent and Trademark Office*